(12) United States Patent
Guo et al.

(10) Patent No.: US 12,181,431 B2
(45) Date of Patent: Dec. 31, 2024

(54) INDIGO-BASED POLYMERS FOR USE IN SWCNTs ELECTRONICS

(71) Applicant: National Research Council of Canada, Ottawa (CA)

(72) Inventors: Chang Guo, Nepean (CA); Jianying Ouyang, Ottawa (CA); Zhao Li, Orleans (CA); Jianfu Ding, Ottawa (CA); Patrick Roland Lucien Malenfant, Ottawa (CA)

(*) Notice: Subject to any disclaimer, the term of this patent is extended or adjusted under 35 U.S.C. 154(b) by 807 days.

(21) Appl. No.: 17/267,184

(22) PCT Filed: Aug. 13, 2019

(86) PCT No.: PCT/IB2019/056871
§ 371 (c)(1),
(2) Date: Feb. 9, 2021

(87) PCT Pub. No.: WO2020/035793
PCT Pub. Date: Feb. 20, 2020

(65) Prior Publication Data
US 2021/0293734 A1 Sep. 23, 2021

Related U.S. Application Data

(60) Provisional application No. 62/718,659, filed on Aug. 14, 2018.

(51) Int. Cl.
*G01N 27/12* (2006.01)
*B82Y 30/00* (2011.01)
(Continued)

(52) U.S. Cl.
CPC ......... *G01N 27/127* (2013.01); *C01B 32/172* (2017.08); *C01B 32/174* (2017.08);
(Continued)

(58) Field of Classification Search
CPC .. G01N 27/127; C01B 32/172; C01B 32/174; C01B 2202/02; C08G 61/124;
(Continued)

(56) References Cited

U.S. PATENT DOCUMENTS 4,151,170 A * 4/1979 Gosteli ................ C09B 7/02
548/426
9,597,677 B2 3/2017 Campidelli et al.
(Continued)

FOREIGN PATENT DOCUMENTS

CN 1871509 A 11/2006
CN 102850527 A * 1/2013
(Continued)

OTHER PUBLICATIONS

Pina et al., Unusual photophysical properties of conjugated, alternating indigo-fluorene copolymers, Journal of Materials Chemistry A, 3(12), 2015, pp. 6373-6382 (Year: 2015).*
(Continued)

*Primary Examiner* — James Lin
*Assistant Examiner* — Vivian A Tran
(74) *Attorney, Agent, or Firm* — Brunet & Co. Ltd.; Robert Brunet; Hans Koenig

(57) ABSTRACT

A compound of Formula (0): where Ar is one or more substituted or unsubstituted aromatic units, R is independently H, F, CN, a $C_1$-$C_{20}$ linear or branched aliphatic group or a $C_1$-$C_{20}$ linear or branched aliphatic acyl group, and n is an integer 3 or greater, is useful for sorting and dispersing carbon nanotubes (CNTs) and for producing printed electronic devices (e.g. $CO_2$ sensors, TFTs) in which the CNTs are functionalized with the compound.

10 Claims, 8 Drawing Sheets

(51) Int. Cl.
    *B82Y 40/00*     (2011.01)
    *C01B 32/172*     (2017.01)
    *C01B 32/174*     (2017.01)
    *C08G 61/12*     (2006.01)
    *B82Y 35/00*     (2011.01)

(52) U.S. Cl.
    CPC ............ *C08G 61/124* (2013.01); *B82Y 30/00* (2013.01); *B82Y 35/00* (2013.01); *B82Y 40/00* (2013.01); *C01B 2202/02* (2013.01); *C08G 2261/124* (2013.01); *C08G 2261/344* (2013.01); *C08G 2261/94* (2013.01)

(58) Field of Classification Search
    CPC ........ C08G 2261/124; C08G 2261/344; C08G 2261/94; B82Y 30/00; B82Y 35/00; B82Y 40/00
    See application file for complete search history.

(56) References Cited

U.S. PATENT DOCUMENTS

| | | |
|---|---|---|
| 2009/0311554 A1 | 12/2009 | Oh et al. |
| 2011/0098591 A1 | 4/2011 | Haick et al. |
| 2012/0118751 A1 | 5/2012 | Cai et al. |
| 2014/0183454 A1 | 7/2014 | Wigglesworth et al. |
| 2017/0122931 A1 | 5/2017 | Carnahan et al. |
| 2017/0200898 A1* | 7/2017 | Noh .................... H10K 85/225 |
| 2017/0350856 A1 | 12/2017 | Kobayashi et al. |

FOREIGN PATENT DOCUMENTS

| | | |
|---|---|---|
| CN | 107151311 A | 9/2017 |
| EP | 1679507 A1 | 7/2006 |
| JP | 862138584 A | 6/1987 |
| JP | 2007103530 A | 4/2007 |
| JP | 2008084786 A | 4/2008 |
| TW | 200504359 A | 3/2005 |
| WO | 2005/040781 A1 | 4/2007 |
| WO | 2018/017699 A1 | 1/2018 |
| WO | 2018/216017 A1 | 11/2018 |

OTHER PUBLICATIONS

Imming et al., An Improved Synthetic Procedure for 6,6'-dibromoindigo (Tyrian Purple), Synthetic Communications, 31(23), pp. 3721-3727 (2001) (Year: 2001).*
Search Report dated Feb. 20, 2023 on Taiwan Application 108128692.
Office Action dated Feb. 20, 2023 on Taiwan Application 108128692.
Glowacki et al. Journal of Materials Chemistry C: Materials for optical, magnetic and electronic devices. 38, 8089-8097 (2014).
Office action dated Nov. 28, 2023 on Japanese application 2021-507607.
International Search Report and Written Opinion dated Dec. 23, 2019 on PCTIB2019/056871.
Liu, Chunchen, Dyes and Pigments, 125, 2016 , 54-63.
Glowacki, E. D. Journal of Materials Chemistry C: Materials for Optical and Electronic Devices, 2(38), 2014, 8089-8097.
Pina, Joao. Journal of Materials Chemistry A: Materials for Energy, 3(12), 2015 , 6373-6382.
Stahl, Thomas. Bioconjugate Chemistry, 28(6), 2017, 1734-1740.
Dubois M, et al. Journal of Colloid and Interface Science 407 (2013) 39-46.
Guo C, et al. Polymer Chemistry. Regioisomeric control of charge transport polarity for indigo-based polymers. Polym. Chem., 2015,6, 6998-7004.
Guo C, et al. J. Mater. Chem. C, 2014, 2, 4289.
Dell'Amico DB, et al. Chem. Rev. 2003, 103, 3857-3897.
Star A, et al. Adv. Mater. 2004, 16(22), 2049-2052.
Sivaramakrishnan S, et al. Sensors and Actuators B 132 (2008) 296-304.
Tulevski GS, et al. ACSNano. 8(9), 8730-8745.
Wang W, et al. Carbon 117 (2017) 263e270.
Zwerneman K. Crit Care Nurs Clin N Am 18 (2006) 217-225.
Zribi A, et al. Sensors and Actuators A 122 (2005) 31-38.
Extended European Search Report dated Jul. 20, 2022 on European application 19849963.4.
Yoon B, et al. ACS Appl. Mater. Interfaces 2018, 10, 33373-33379.
Star A, et al. Adv. Mater. 2004, 16, No. 22, 2049-2052.
Hannon A, et al. Sensor Letters vol. 12, 1469-1476, 2014.

* cited by examiner

INDIGO-BASED POLYMERS FOR USE IN SWCNTs ELECTRONICS

FIELD

This application relates to indigo-based compounds and the use of indigo-based compounds for use in printable electronics (PE). In particular, the compounds can be used to make carbon dioxide ($CO_2$) gas sensors that include carbon nanotube-based sensor elements, and to make thin film transistors (TFTs) based on semiconducting single-walled carbon nanotubes (sc-SWCNTs).

BACKGROUND $CO_2$ levels can be used to estimate indoor air quality and as an essential respiratory indicator for capnography. Current $CO_2$ measurement systems like infra-red analyzers (e.g. non-dispersive infra-red (NDIR)) and mass spectrometers are undesirable due to high cost and lack of portability.

Carbon nanotube (CNTs) based sensors have the potential to be inexpensive and portable. The large surface area of CNTs holds promise in lowering the detection limit of sensors based thereon. However, CNTs are poorly responsive to weak Lewis acids or bases like $CO_2$. Modification of CNTs with functional chemical groups is one avenue to increasing the responsiveness of CNTs-based sensors. While CNTs themselves barely interact with $CO_2$, CNTs can interact with primary and secondary amines even under normal conditions of temperature and pressure. To achieve $CO_2$ sensitivity, CNTs are usually chemically functionalized or coated with a polyethyleneimine (PEI) film to introduce amine groups on the CNTs. The amine groups selectively change the resistivity of CNTs in the presence of $CO_2$. However, sensitivity of such functionalized CNTs to $CO_2$ remains unsatisfactory.

Further, printable electronics, especially printable thin film transistors (TFTs) and sensors, have been widely studied in the last 20 years due to their low cost and facile processability over a large area. To print high performance electronics with a good yield, the development of inks has become one of the most critical technologies in this area. Semiconducting single-walled carbon nanotubes (sc-SWCNTs) are preferred as channel semiconductors for printable electronics since they have excellent electrical performance, stable chemical and physical properties and good dispersion in organic solvents. However, most as-produced SWCNTs are a mixture of metallic carbon nanotubes (m-SWCNTs) and semiconducting carbon nanotubes (sc-SWCNTs) and tend to aggregate and then form tube bundles in solution. Therefore, pristine SWCNTs cannot be directly used as inks to print high performance electronics.

In recent years, conjugated polymer extraction (CPE) processing has become a very reliable method to obtain high purity sc-SWCNTs from as-produced raw materials. The easy, scalable and low-cost process makes CPE highly desirable for industrial manufacturing compared to other surfactant-based methods. The product obtained from CPE with high concentration (up to 50%) dispersion of tubes is usually dispersed stably in organic solvents, which can be readily used as inks for inkjet or roll-to roll printing. Currently, conjugated polymers used to sort and disperse sc-SWCNTs are only based on a few homo/co-polymers such as polyfluorene, polycarbazole and polythiophene derivatives.

There still remains a need for carbon nanotube-based sensor elements that have improved sensitivity to $CO_2$ and a need for improving dispersion and separation of sc-SWCNTs from m-SWCNTs to provide sc-SWCNTs inks for use in high performance printable electronics.

SUMMARY

It has now been found that CNTs functionalized with certain indigo-based compounds provide sensors that have excellent sensitivity to $CO_2$. The indigo unit has secondary amine groups that can interact with $CO_2$ to provide $CO_2$ sensors exhibiting good performance. The secondary amines react with $CO_2$ to change electrical conductance of the CNTs, which can be measured to provide an estimate of $CO_2$ concentration.

In one aspect, there is provided a $CO_2$ sensor comprising: an electrode pair; and, an electrically conductive sensing material in contact with the electrode pair, the sensing material comprising a film of CNTs functionalized with a compound of Formula (I):

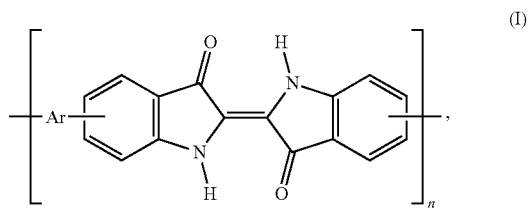

where Ar is one or more substituted or unsubstituted aromatic units and n is an integer 3 or greater, the compound of Formula (I) interacting with $CO_2$ to change electrical conductance of the CNTs by an amount that correlates to $CO_2$ concentration.

The sensors of the present invention are useful for measuring $CO_2$ levels or changes in $CO_2$ levels in an environment. The sensors are particularly useful for respiratory $CO_2$ monitoring in clinical settings (e.g. in capnography) and indoor air quality estimation. The sensors are less expensive to fabricate and portable in comparison to state-of-the-art $CO_2$ sensor systems such as infra-red analyzers and mass spectrometers. The sensors show better sensitivity (about 3% to 1200 ppm $CO_2$ in air with relative humidity (RH) ~40%) in comparison to non-functionalized CNTs.

In another aspect, there is provided a process for producing a compound of Formula (I) comprising thermally decomposing a compound of Formula (Ia):

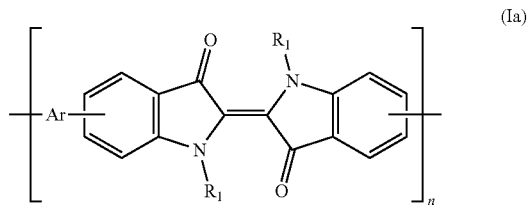

at a temperature of 160° C. or greater, where Ar and n are as defined for the compound of Formula (I) and each $R_1$ is a thermocleavable protecting group.

It has also now been found that certain indigo-based compounds provide for highly efficient SWCNT purification, dispersion and TFT fabrication. The indigo-based compounds sort and disperse sc-SWCNTs with high efficiency, and the resulting organic solutions can be directly used as an ink for PE.

In another aspect, there is provided a process for sorting and dispersing SWCNTs, the process comprising: extracting a mixture of sc-SWCNTs and m-SWCNTs with a compound of Formula (II):

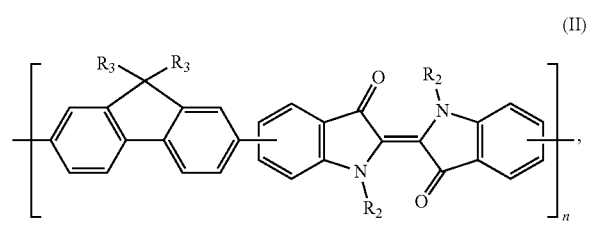

where: n is an integer 3 or greater; each $R_2$ is independently H, F, CN, a $C_1$-$C_{20}$ linear or branched aliphatic group or a $C_1$-$C_{20}$ linear or branched aliphatic acyl group; and, each $R_3$ is independently a $C_{1-36}$ linear or branched alkyl group, to produce an enriched sc-SWCNT dispersion; and, separating undispersed m-SWCNTs from the enriched sc-SWCNT dispersion.

In another aspect, there is provided a printed electronic device comprising a film of sc-SWCNT extracted by a compound of Formula (II):

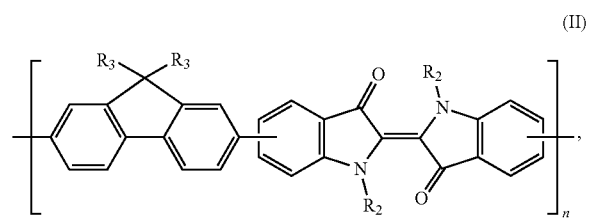

where: n is an integer 3 or greater; each $R_2$ is independently H, F, CN, a $C_1$-$C_{20}$ linear or branched aliphatic group or a $C_1$-$C_{20}$ linear or branched aliphatic acyl group; and, each $R_3$ is independently a $C_{1-36}$ linear or branched alkyl group.

In another aspect, there is provided a novel compound of Formula (III):

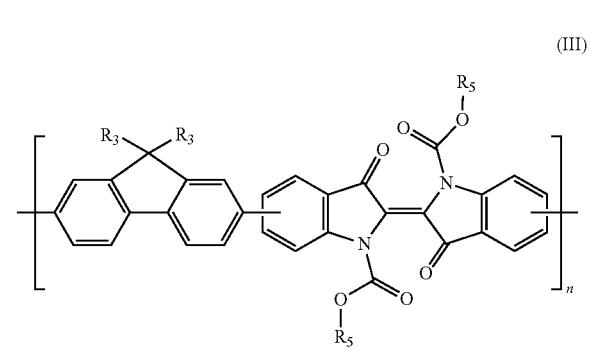

where n is an integer 3 or greater, each $R_3$ is independently a $C_{1-36}$ linear or branched alkyl group and $R_5$ is a $C_{1-4}$ alkyl group. $R_5$ is preferably t-butyl.

Further features will be described or will become apparent in the course of the following detailed description. It should be understood that each feature described herein may be utilized in any combination with any one or more of the other described features, and that each feature does not necessarily rely on the presence of another feature except where evident to one of skill in the art.

BRIEF DESCRIPTION OF THE DRAWINGS

For clearer understanding, embodiments will now be described in detail by way of example, with reference to the accompanying drawings, in which.

DETAILED DESCRIPTION

Figure 1:
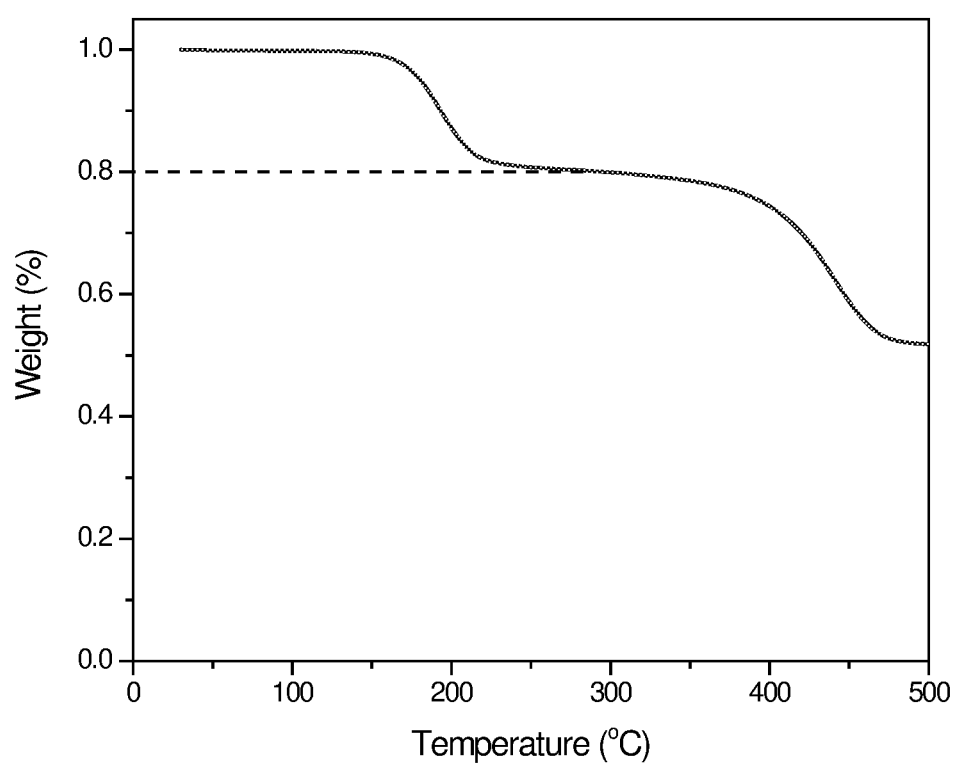
FIG. 1 is a thermogravimetric analysis (TGA) curve of PFIDBu at a heating rate of 10° C. per minute under nitrogen gas showing the thermal decomposition of PFIDBu to PFID.

A compound of Formula (0):

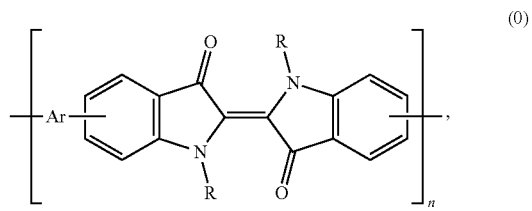

where Ar is one or more substituted or unsubstituted aromatic units, R is independently H, F, CN, a $C_1$-$C_{20}$ linear or branched aliphatic group or a $C_1$-$C_{20}$ linear or branched aliphatic acyl group, and n is an integer 3 or greater, is useful for sorting and dispersing carbon nanotubes (CNTs) and for producing printed electronic devices (e.g. $CO_2$ sensors, TFTs) in which the CNTs are functionalized with the compound.

$CO_2$ Sensors

The sensing material comprises a film of CNTs functionalized with an indigo compound of Formula (I). The compound of Formula (I) interacts with $CO_2$ to change electrical conductance of the CNTs by an amount that correlates to $CO_2$ concentration.

The compound of Formula (I) is:

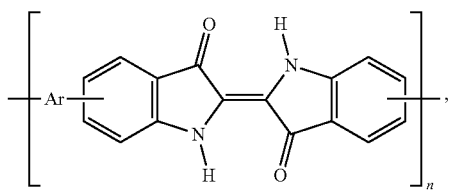

(I)

where Ar is one or more substituted or unsubstituted aromatic units and n is an integer 3 or greater. The compound of Formula (I) has alternating Ar and indigo units. The Ar unit may be bonded to the indigo unit at the 4, 4' or 5, 5' or 6, 6' or 7, 7' positions of the indigo unit. The integer n is preferably no greater than 60, more preferably in a range of 3-50 or 20-50. The compound is preferably a polymer having a number average molecular weight ($M_n$) greater than about 3,000 Da, for example from about 3,000 Da to about 500,000 Da, preferably from about 3,000 Da to about 50,000 Da or about 10,000 to about 50,000. The secondary amine groups on the compound of Formula (I) can interact with $CO_2$ to influence electrical conductance of the CNTs by an amount that correlates to $CO_2$ concentration.

Ar is one or more substituted or unsubstituted aromatic units. In an embodiment, Ar in the compound of Formula (I) is one or more of an indigo, a fluorene, a thiophene, a phenylenevinylene, a bithiophene, a phenylene, a bipyridine, an anthracene, a naphthalene or a benzothiadiazole. Ar is preferably a fluorene, for example a 9,9-dialkyl-substituted fluorene, where each substituent is independently a $C_{1-36}$ linear or branched alkyl group, preferably a $C_{10-36}$ linear or branched alkyl group, more preferably a $C_{10-18}$ linear or branched alkyl group.

Compounds of Formula (I) may be produced by any suitable process. In one embodiment, the one or more substituted or unsubstituted aromatic units from which Ar is derived may be functionalized with an appropriate leaving group and the functionalized substituted or unsubstituted aromatic units reacted with halogenated indigo units as illustrated in Scheme 1, where: Ar and n are as described for Formula (I); L is a leaving group, for example dioxaborolane; X is a halogen, for example Br, Cl or I, preferably Br; and, $R_4$ is H or a thermocleavable protecting group (e.g. t-Boc). The process in Scheme 1 may be catalyzed with a metal catalyst (e.g. $Pd(PPh_3)_4$) in a suitable solvent (e.g. toluene, butanol and/or water) under an inert atmosphere (e.g. nitrogen, argon) for a suitable length of time (e.g. 6-96 hours) at an elevated temperature (e.g. 50-150° C.) under suitable conditions of pH (e.g. in the presence of a base such as an alkali metal carbonate) to produce the compound of Formula (I) where $R_4$ is H or a like compound where $R_4$ is the thermocleavable protecting group. The compound may be isolated by known techniques. The process may be adapted from the process as described in Pina et al. (*J. Mater. Chem. A*, 2015, 3, 6373-6382), which is herein incorporated by reference.

Scheme 1

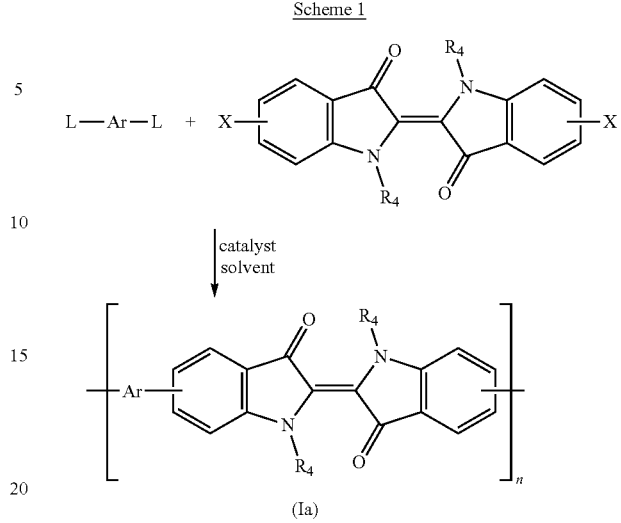

Where $R_4$ in the compound produced in Scheme 1 is the thermocleavable protecting group, the protecting group may be removed by annealing the compound at an elevated temperature to decompose the protecting group and provide the compound of Formula (I) containing secondary amine groups where $R_1$ is H. The annealing temperature is preferably 160° C. or greater, more preferably a temperature in a range of 160° C. to 350° C. The use of a thermocleavable protecting group, especially an alkyloxycabonyl group, is advantageous to increase the solubility of the indigo units for reaction with the substituted or unsubstituted aromatic units. Lower alkyloxycabonyl groups, for example $C_{1-4}$alkyloxycarbonyl groups, are particularly preferred. $C_{1-4}$alkyloxycarbonyl groups having greater steric hindrance, for example tert-butyloxycarbonyl (t-Boc) groups, are particularly preferred.

The CNTs are metallic or semiconductors. The CNTs may be SWCNTs, multiwalled (MWCNTs) or few-walled (FWCNTs). The CNTs may come from any convenient source of CNTs preparation. In one embodiment, SWCNTs are preferred. The SWCNTs may comprise raw (about 0.6 to 2.2 nm average diameter) SWCNTs prepared from HiPco, CoMoCAT, CVD, arc-discharge, laser-ablation or plasma processes.

Films of the sensing material may be prepared from the CNTs and the compound by any suitable method. For example, the compound may be mixed with the CNTs in a solvent, preferably an organic solvent especially an aromatic solvent such as toluene, benzene, ethyl benzene, chlorobenzene, dichlorobenzene, trichlorobenzene, xylenes, 1-methylnaphthalene and mixtures thereof, to form a mixed solution, followed by ultrasonication of the mixed solution and separation of the solution from particulate precipitate using a centrifugal separator. The amount of compound present in the solution in relation to the amount of CNTs (i.e. compound:CNT mass ratio) is preferably about 0.25:1 or greater, for example about 0.25:1 to 10:1. Ultrasonication may be performed, for example, at about 15 to 50 Hz for about 30 to 60 minutes. Centrifugal separation may be performed, for example, at about 8,000 to 10,000 g. Supernatant from centrifugal separation may then be utilized to form a film of CNTs functionalized by the compound. Film forming techniques are generally known in the art and include, for example, spin-coating, doctor blading, casting and the like.

In one embodiment, the sensing material may comprise 0.0001 to 0.05 mg/ml of CNTs contained in the compound.

To fabricate a sensor, a film of the sensing material is brought into contact with an electrode pair comprising a first electrode and a second electrode. The film of sensing material may be pre-formed and then contacted with and adhered to each of first and second electrodes in the electrode pair. The film of sensing material may be formed in the presence of the electrode pair so that the film of sensing material forms on the electrode pair to produce a unitized structure.

For example, the film of sensing material may be formed on the electrode pair by immersing a substrate having the electrode pair thereon in an ink containing sensing material and then drying the ink to form the film of sensing material on the electrode pair. Immersion may be performed for any suitable length of time, for example about 5 minutes or more, or about 30 minutes or more. Generally, no more than about 1-2 hours of immersion are required. After drying, the substrate with the film of sensing material may be washed in a suitable solvent (e.g. an alcohol such as isopropanol) then thermally annealed. Thermal annealing may be performed at any suitable temperature and length of time, for example at a temperature in a range of about 150-250° C. for a time in a range of about 5-60 minutes.

In operation, the electrodes are connected in an electrical circuit to a source of electricity and electrical current is passed between the first and second electrodes through the sensing material by virtue of the conductive properties of the CNTs. A current or resistance meter is connected in the circuit to measure current or resistance. When the sensing material is exposed to $CO_2$, the compound of Formula (I) interacts with the $CO_2$ through the secondary amine group, thereby changing the electrical resistance of the CNTs, the change being measured as a change in current or a change in resistance in the circuit. As $C_{O2}$ concentration around the sensor changes, the change in $CO_2$ concentration is reflected in a change of current or resistance in the circuit. Generally, an increase in $CO_2$ concentration results in an increase in resistance.

The sensor may include various components typically found in transistors or chemiresistors for chemical sensors, for example a dielectric substrate on which the sensing material and electrode pair may be supported, a $CO_2$-permeable insulating layer, a source electrode, a drain electrode, a gate electrode, a heater, a porous membrane, organic or inorganic electrolytes and the like.

Sorting and Dispersing SWCNTs for Use in Printed Electronic Devices

Mixtures of sc-SWCNTs and m-SWCNTs can be extracted with the compound of Formula (II):

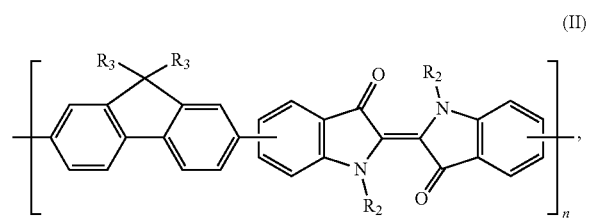

(II)

to produce an enriched sc-SWCNT dispersion. The extraction provides both high yield and purity of sc-SWCNTs, therefore the enriched sc-SWCNT dispersion can be used directly as an ink for producing printed electronics, especially thin film transistors (TFTs).

The compound of Formula (II) has alternating fluorene and indigo units. The fluorene unit may be bonded to the indigo unit at the 4, 4' or 5, 5' or 6, 6' or 7, 7' of the indigo unit.

In the compound of Formula (II), each $R_2$ is independently H, F, CN, a $C_1$-$C_{20}$ linear or branched aliphatic group or a $C_1$-$C_{20}$ linear or branched aliphatic acyl group. In some embodiments, each $R_2$ is the same. Preferably, $R_2$ is a $C_1$-$C_{20}$ linear or branched aliphatic acyl group. In some embodiments, the linear or branched aliphatic group or linear or branched aliphatic acyl group has 1-8 carbon atoms. Lower alkyloxycabonyl groups, for example $C_{1-4}$alkyloxycarbonyl groups, are particularly preferred. $C_{1-4}$alkyloxycarbonyl groups having greater steric hindrance, for example tert-butyloxycarbonyl (t-Boc) groups, are particularly preferred.

In the compound of Formula (II), each $R_3$ is independently a $C_{1-36}$ linear or branched alkyl group, preferably a $C_{10-36}$ linear or branched alkyl group, more preferably a $C_{10-18}$ linear or branched alkyl group.

In the compound of Formula (II), n is an integer 3 or greater. The integer n is preferably no greater than 60, more preferably in a range of 3-50 or 20-50. The compound is preferably a polymer having a number average molecular weight ($M_n$) greater than about greater than about 3,000 Da, for example from about 3,000 Da to about 500,000 Da, preferably from about 3,000 Da to about 50,000 Da or about 10,000 to about 50,000.

The mixture of sc-SWCNTs and m-SWCNTs may come from any convenient source of CNTs preparation. Such starting material preferably comprises raw (about 0.6 to 2.2 nm average diameter) SWCNTs prepared from HiPco, CoMoCAT, CVD, arc-discharge, laser-ablation or plasma processes. The amount of compound used in the extraction in relation to the amount of SWCNTs in the mixture of sc-SWCNTs and m-SWCNTs (i.e. compound:SWCNT mass ratio) is preferably about 0.25:1 or greater, for example 0.25:1 to 10:1.

In order to enhance the selectivity, extracting with the compound is preferably accomplished in a non-polar solvent. The non-polar solvent preferably comprises an organic solvent, more preferably an organic aromatic solvent. Some examples of non-polar solvents include, for example, toluene, benzene, ethyl benzene, chlorobenzene, dichlorobenzene, trichlorobenzene, xylenes, 1-methylnaphthalene and mixtures thereof. Toluene is preferred. The mixture of sc-SWCNTs and m-SWCNTs may be dispersed in the solvent in the presence of the compound. The mixture of sc-SWCNTs and m-SWCNTs is preferably dispersed in the solvent at a concentration of from about 0.1 mg/mL to about 10.0 mg/mL, preferably about 0.4 mg/mL to about 2.0 mg/mL, with a compound/SWCNTs ratio of 0.5:1 to 10:1. The compound/SWCNTs ratio may significantly impact the extraction yield and sc-purity. A high ratio will produce a high yield but a low purity. After mixing, the mixture is preferably allowed to interact for a period of time from 5 min to 5 h, preferably 10 to 60 min. Formation of the dispersion may be assisted by known techniques in the art, for example, sonication, mechanical agitation and the like. Tip sonication is preferred.

Subsequent separation of the well-dispersed SWCNTs from the poorly-dispersed SWCNTs collects compound-coated SWCNTs in the dispersion, while undispersed non-coated SWCNTs are removed. The subsequent separation may be accomplished by any suitable method, for example centrifugation, filtration and the like, or any combination thereof. Centrifugation is preferred. Such centrifugation typically yields sediment and supernatant, the sediment having gravitated to the bottom of a centrifuge tube and the supernatant being the liquid on top. The sediment is enriched in m-SWCNTs and the supernatant is enriched in sc-SWCNTs, relative to the starting mixture. Because the conjugated compound selectively interacts with the sc-SWCNTs to keep them dispersed, the SWCNTs remaining in the dispersion (e.g. in the supernatant) after separation are enriched in sc-SWCNTs, while the SWCNTs separated from the dispersion (e.g. in the sediment) are enriched in m-SWCNTs. More extraction processes can be applied to the sediment and the resulting combination dispersion will give a higher yield of sc-SWCNTs.

For example, enrichment yield may reach 21% (based on the amount of sc-SWCNT in raw CNT nanotubes) after six extractions, depending on the solvent used. The presence of a small amount of a polar solvent is able to either significantly increase the yield with comparable purity or greatly shorten the process. For instance, the yield may reach 17% after three extractions with the presence of 1% tetrahydrofuran or the yield may reach 12% after two extractions with the presence of 1% methyl carbitol. The sc-purity of the enriched SWCNTs is very high, for example as high as 99.9%, and the tiny amount of m-SWCNTs in the enriched SWCNTs can be removed by silica gel adsorption.

The enriched sc-SWCNT dispersion can be used directly as an ink for producing printed electronics. In producing the printed electronic device, the ink may be deposited on a substrate by any suitable method, for example, roll-to-roll printing, screen printing, inkjet printing, flexography printing, gravure printing, off-set printing, airbrushing, aerosol printing, typesetting, stamp or any other method. The ink is particularly suited to ink jet and roll-to-roll printing.

Printable substrates useful in printed electronic devices are generally known and include, for example polyethylene terephthalate (PET) (e.g. Melinex™), amorphous polyethylene terephthalate (APET), glycol modified polyethylene terephthalate (PET-G), polyethylene naphthalate, polyolefin (e.g. silica-filled polyolefin (Teslin™)) polydimethylsiloxane (PDMS), polystyrene, polycarbonate, polyimide (e.g. Kapton™) thermoplastic polyurethane (TPU), acrylonitrile/butadiene/styrene, polystyrene, silicone membranes, wool, silk, cotton, flax, jute, modal, bamboo, nylon, polyester, acrylic, aramid, spandex, polylactide, textiles (e.g. cellulosic textiles), paper, glass, metal, dielectric coatings, among others.

Printed electronic devices include, for example, electrical circuits, conductive bus bars (e.g. for photovoltaic cells), sensors (e.g. touch sensors, wearable sensors), antennae (e.g. RFID antennae), thin film transistors (TFT), diodes, smart packaging (e.g. smart drug packaging), conformable inserts in equipment and/or vehicles, and multilayer circuits and MIM devices including low pass filters, frequency selective surfaces, transistors and antennas. Thin film transistors (TFT) are of particular note.

EXAMPLES

Example 1—Synthesis of PFIDBu (IV)

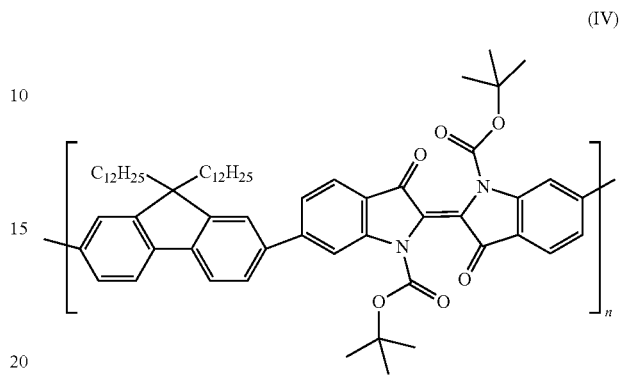

To help solubilize indigo monomers for co-polymerization with 9,9-diduodecyl-fluorene monomers, thermocleavable side chains of tert-butyloxycarbonyl (t-Boc groups) were introduced on to the amine nitrogen atoms of the indigo monomers and then the substituted indigo monomers were copolymerized with 9,9-diduodecyl-fluorene monomers to produce poly(9 9-di-n-octylfluorenyl-2 7-diyl-alt-1,1'-diisobutyloxy-2,2' biindolinyldene-3,3-dione-diyl-6,6') (PFIDBu) (IV).

To a 100 mL three-necked flask was added 0.62 g di-tert-butyl 6,6'-dibromo-3,3'-dioxo-[2,2'-biindolinylidene]-1,1'-dicarboxylate, 0.75 g 2,7-dibromo-9,9-didodecylflourene and 5 drops of Aliquat™ 336. The flask was degassed and refilled with argon for 20 min before addition of 30 mL dry toluene and 46.6 mg Pd(PPh$_3$)$_4$. Subsequently, 12.5 mL of degassed 2 M Na$_2$CO$_3$ solution was added and the reaction flask was sealed. The mixture was stirred for 72 h at 95° C. Upon cooling to room temperature, the mixture was added to vigorously stirred methanol (200 mL), filtered and washed with methanol. The resulting precipitate was purified by Soxhlet extraction with acetone, hexane and chloroform.

Example 2—Synthesis of PFID (V)

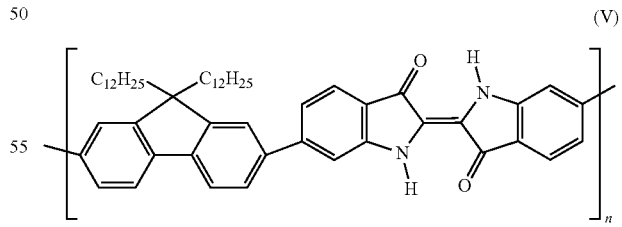

The copolymer poly(9 9-di-n-octylfluorenyl-2 7-diyl-alt-2,2' biindolinyldene-3,3-dione-diyl-6,6') (PFID) (V) was produced by thermally annealing PFIDBu (IV) at 200° C. for 30 min to decompose the thermocleavable t-Boc groups from (IV) resulting in the formation of secondary amine groups in PFID (V).

FIG. 1 shows a thermogravimetric analysis (TGA) curve produced when PFIDBu (IV) is heated at a heating rate of 10° C. per minute under nitrogen gas. After 160° C., the PFIDBu (IV) thermally decomposes into PFID (V). PFIDBu (IV) started to lose weight at about 160° C. until the weight loss plateaued at about 20%. The 20% weight loss coincides with the calculated mass of the t-Boc groups (about 20%) in PFIDBu (IV).

Figure 2:
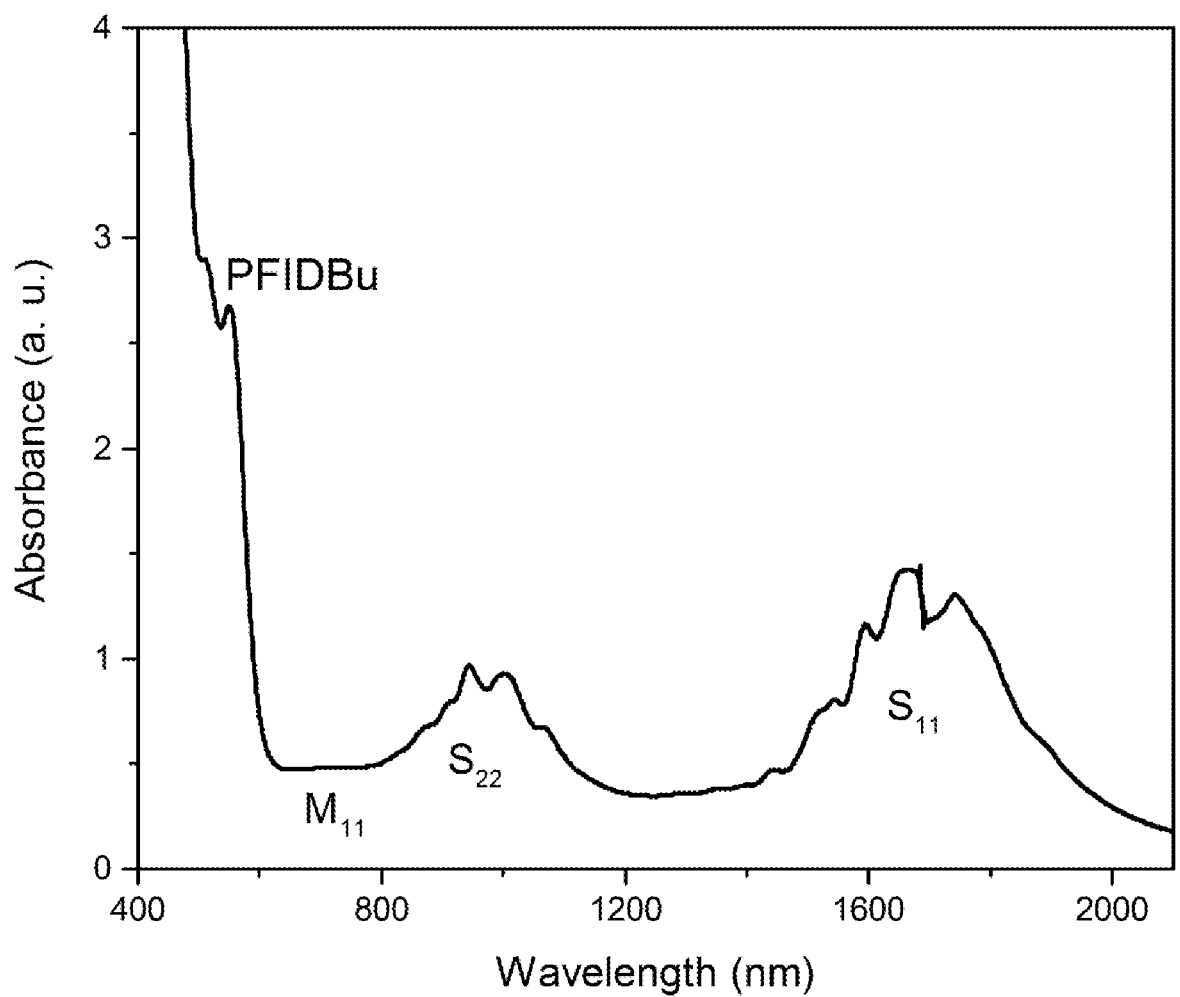
FIG. 2 is an absorption spectrum of a PFIDBu wrapped sc-SWCNT dispersion.

The combined result of Examples 1 and 2 is the synthetic Scheme 2:

2. As seen in FIG. 2, the sc-SWCNT was well dispersed as indicated by the well resolved CNT S11 and S22 bands. The sc-SWCNT purity was very high as confirmed by the invisible M11 band. Two PFIDBu polymer peaks (minor) also present at about 510 nm and about 505 nm are also evident in the spectrum.

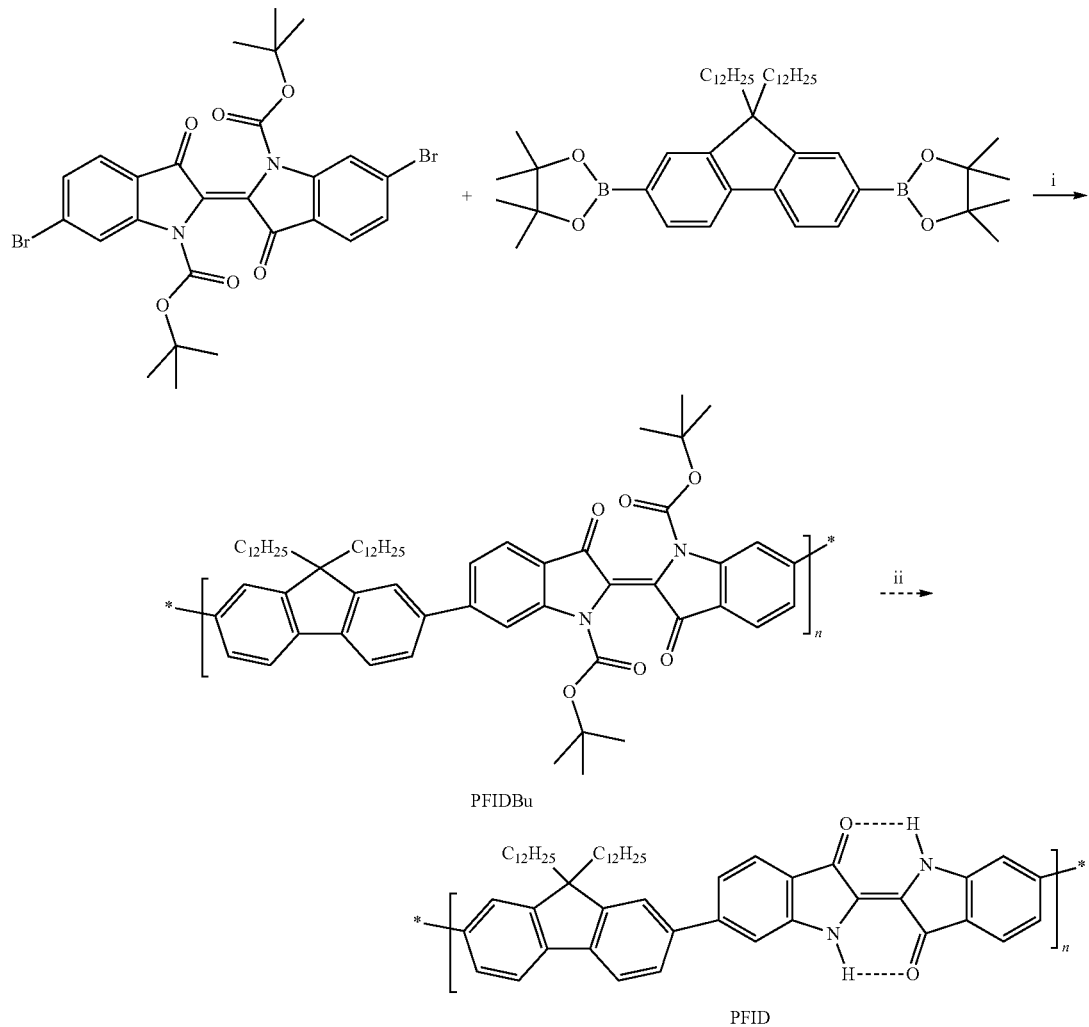

The chemical structures represent the indigo-based polymer PFIDBu as used to provide PFID for use Example 5.

Example 3—Extraction and Dispersion of SWCNTs 3.2 mg PFIDBu (IV) was mixed with 6.4 mg raw plasma tubes in 8 mL toluene with 1 wt % of methyl carbitol (which could be in a range of 0.5-3.6%). After 30 min tip sonication, the mixture was centrifuged at 18700 g for 30 min and the supernatant was collected. 3.2 mg polymer was then mixed with the precipitates and the process was repeated till the metallic feature was obvious in the absorption spectra of the supernatants.

The interaction between PFIDBu (IV) and sc-SWCNTs is quite strong as evidenced by the absorption spectrum of FIG.

Example 4—Preparation of Thin Film Transistors (TFTs

Figure 3:
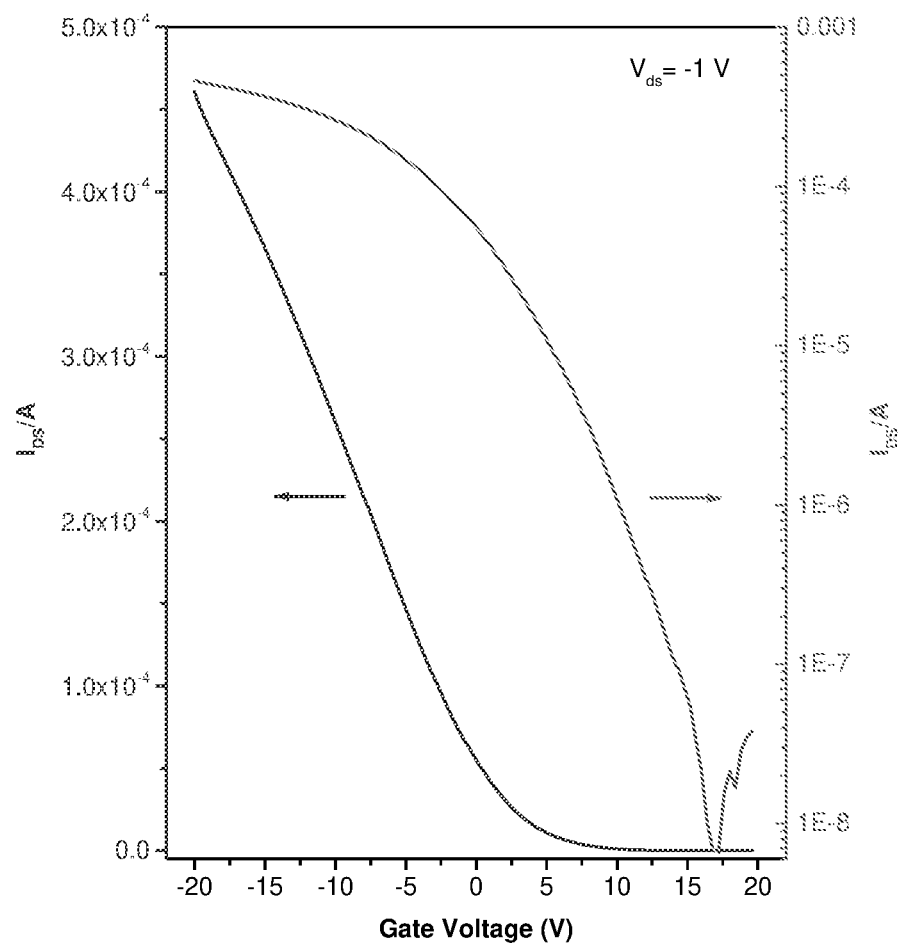
FIG. 3 is a plot of transistor characteristics from a random network of sc-SWCNT with a channel length/width of 10/2000 μm.

The PFIDBu (IV)/sc-SWCNT dispersions from Example 3 have stable dispersity and suitable viscosity for use as an ink jet ink. A TFT was prepared by ink jetting the dispersion from Example 3 on to a $SiO_2$ substrate using a Konica Minolta (KM-512) printer head. As seen in FIG. 3, an inkjet printed PFIDBu (IV)/sc-SWCNT (50 mg L-1, 3:1) channel on $SiO_2$ (100 nm)/Si substrate showed mobility of up to 9 $cm^2$ $V^{-1}$ $s^{-1}$ and on/off current ratios >105.

The thin film transistors were fabricated on commercially available Fraunhofer chips. Prior to the printing of the dispersion from Example 3, chips were bath sonicated for 20 min each in acetone and isopropanol followed by 30 min in UV-Ozone. The PFIDBu (IV)/sc-SWCNT ink (50 mg/L with 3:1 polymer/tube ratio) was ink-jet printed over the channel using a Konica Minolta™ (KM-512). The chips were rinsed with isopropanol and then thermal annealed at 200° C. for 30 min. TFTs with inkjet printed PFIDBu (IV)/sc-SWCNT channels on $SiO_2$ exhibit effective mobilities of about 9 $cm^2$ $V^{-1}$ $s^{-1}$ and on/off ratios of about 105.

Example 5—Preparation and Performance of $CO_2$ Sensors

We found that indigo based polymers (structure shown in Formula I) can be used for making CNT-based $CO_2$ sensors.

Figure 4:
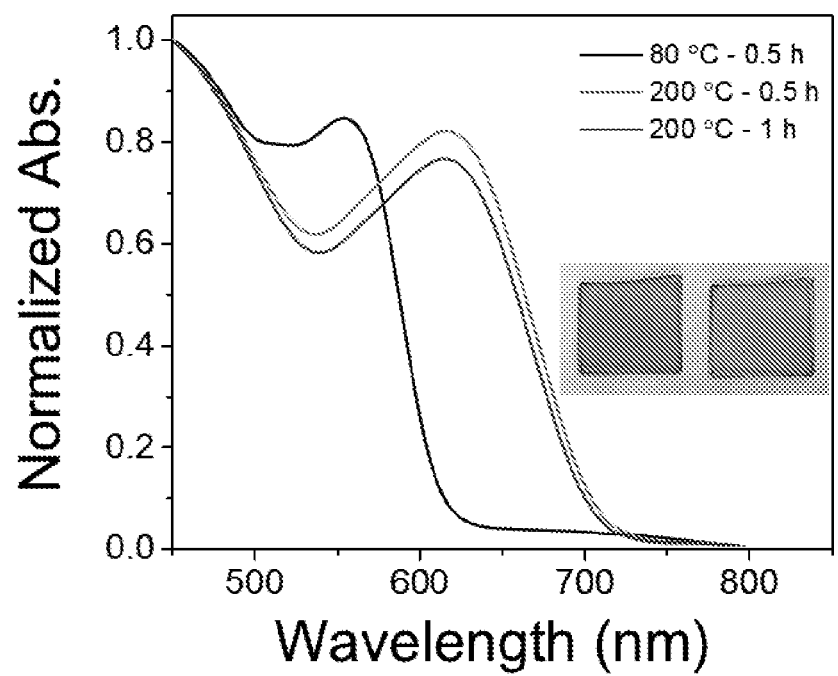
FIG. 4 UV-vis absorption spectra of PFIDBu films on glass substrates annealed at different temperature and different periods of time.

The indigo-based polymer PFIDBu of Scheme 2 was used for Example 5. The reagents and conditions applied were: (i) $Pd(PPh_3)_4$/Aliquat 336/$K_2CO_3$/95° C.; and (ii) heating at >160° C. After thermal annealing at >160° C., the side chains (t-Boc groups) could be decomposed to obtain both PFIDBu and PFID (see FIG. 1). The polymer started to lose weight at ~160° C. and reached a region with a weight loss of ~20%. This weight loss coincided with the calculated mass of the t-Boc groups (~20%) in PFID. The spectra of the polymer films annealed at 200° C. for 0.5 h and 1 h remained very similar, indicating the complete removal of t-Boc groups within 30 min (FIG. 4). The resulting secondary amine groups can interact with $CO_2$ molecules. The change of the polymer's electronic properties will disturb the conductance of CNTs, which can be easily detected in a two or three terminal device (chemiresistor or transistor).

For comparison, a sensor chip was fabricated from poly (9,9-di-n-dodecylfluorene (PFDD) wrapped CNTs in a similar manner as described above. The prepared substrate with printed electronics was immersed in the ink for 10 min, and then rinsed with isopropanol, followed by thermal-annealing at 200° C. for 30 min.

The sensors produced were tested for performance. The prepared sensor chip was placed into a chamber (volume about 20 mL) mounted with an Ossila circuit board. The concentration of the input gas ($CO_2$) was controlled by two mass flow controllers at 400, 800, 1200, 1600 and 2000 ppm in air.

Figure 5:
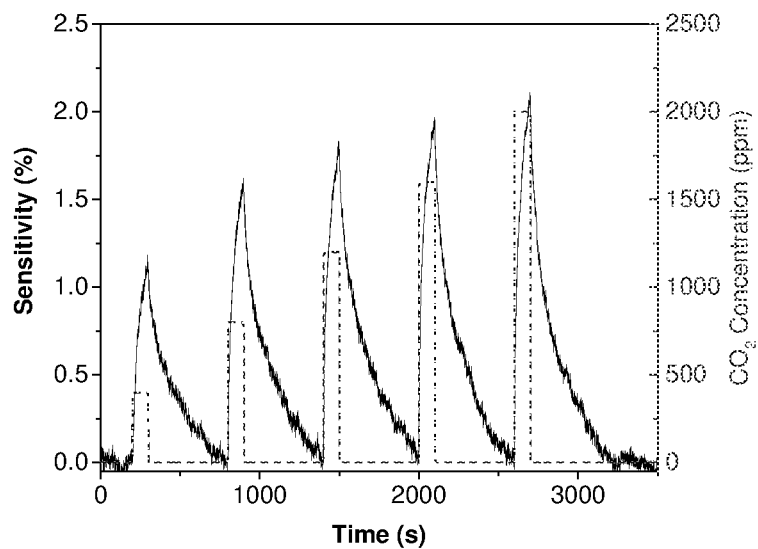
FIG. 5 is a graph of $CO_2$ concentration (ppm) vs. time (s) showing the sensitivity (%) of a PFID functionalized CNTs-based sensor to various $CO_2$ concentrations up to 2000 ppm $CO_2$ in dry air.
Figure 6:
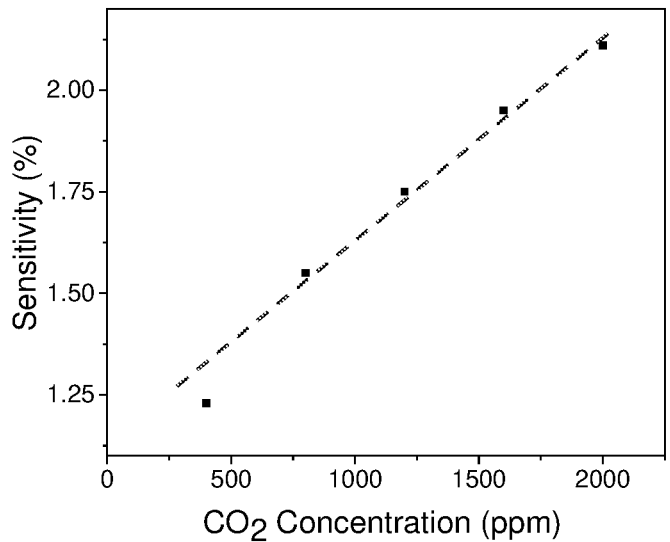
FIG. 6 Linear response of the sensor to 400-2000 ppm $CO_2$ in dry air.

The sensor based on PFID functionalized CNTs exhibits a staircase and linear response (sensitivity up to about 2%) to $CO_2$ every 400 ppm from 400 to 2000 ppm $CO_2$ in dry air (see FIGS. 5 and 6).

Figure 7:
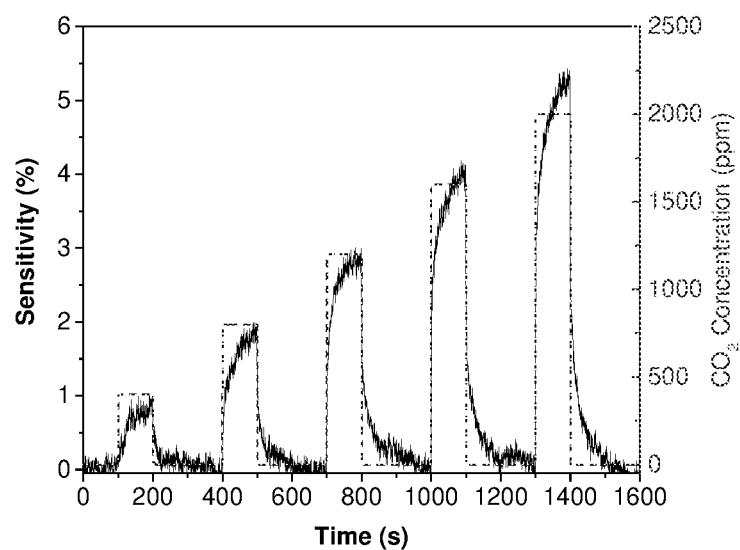
FIG. 7 Response of PFID functionalized CNTs sensor to various $CO_2$ concentrations in air with RH~40%.
Figure 8:
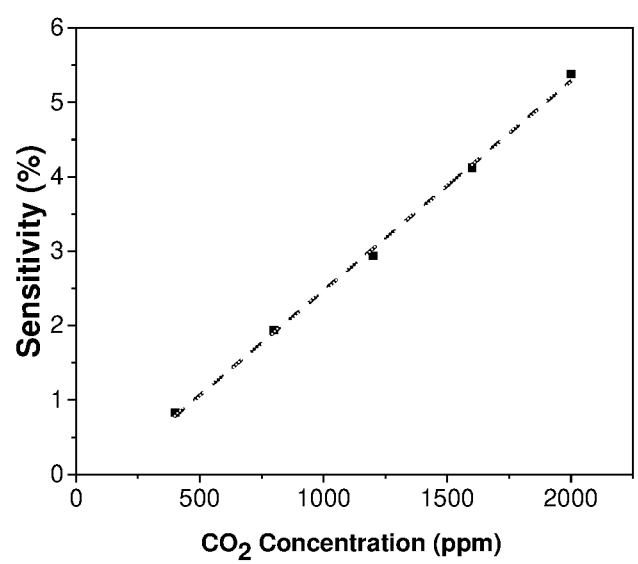
FIG. 8 Linear response of the sensor to 400-2000 ppm $CO_2$ in air with RH~40%.
Figure 9:
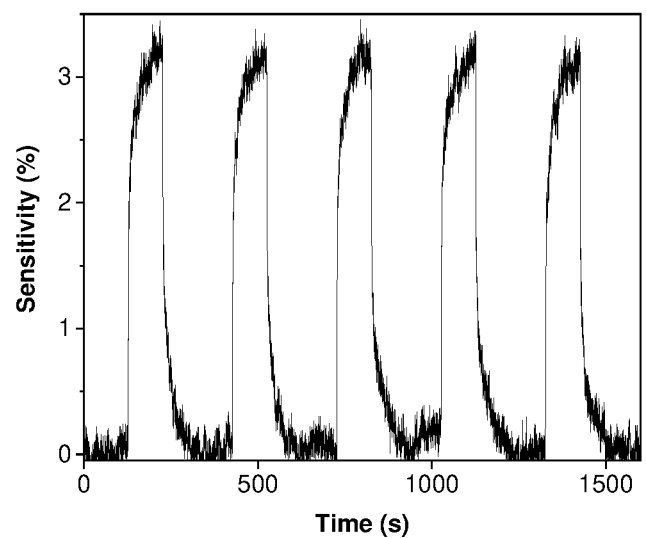
FIG. 9 Stable response of the sensor to 1200 ppm $CO_2$ in air with RH~40%.
Figure 10:
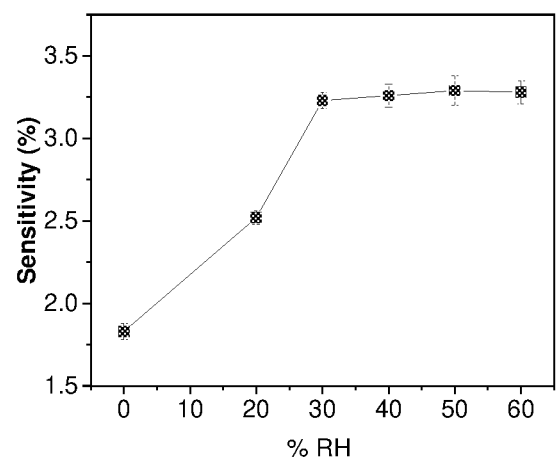
FIG. 10 The sensor response to 1200 ppm $CO_2$ in air with the increase of RH.

In air with relative humidity (RH)~40%, the sensor based on PFID functionalized CNTs showed linear responses (sensitivity up to ~5.4%) to $CO_2$ from 400 to 2000 ppm by every 400 ppm (see FIGS. 7 and 8). When the sensor was exposed to 1200 ppm $CO_2$ gas under the same condition, the response and recovery time, as well as the sensitivity didn't show obvious change after 5 cycles, indicating the good stability of the sensor. (FIG. 9) The response to $CO_2$ increased with the rise of RH, but reached saturation when the RH reached 30%. (FIG. 10)

Figure 11A:
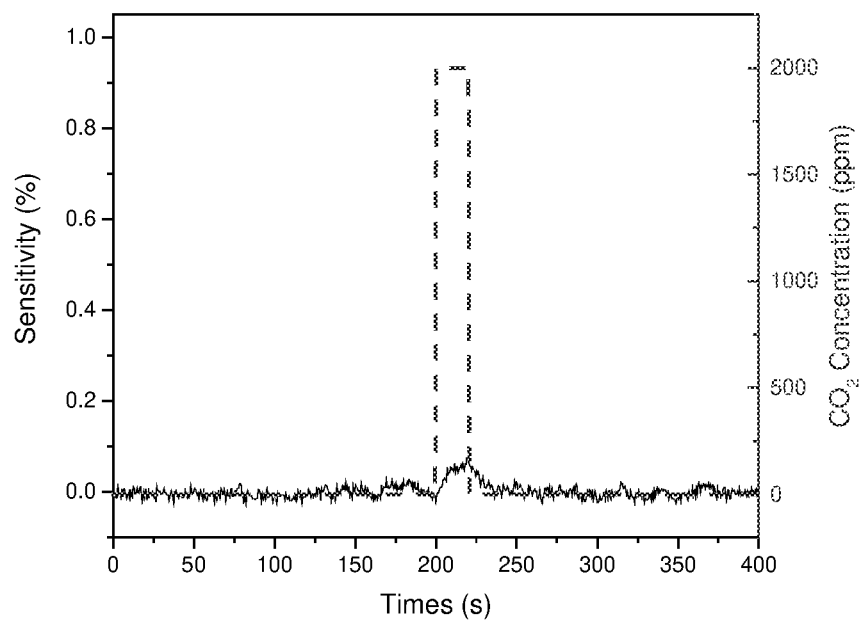
FIG. 11 a) is a graph of $CO_2$ concentration (ppm) vs. time (s) showing the sensitivity (%) of a bare CNTs-based sensor up to 2000 ppm $CO_2$. and b) Response of bare CNTs sensor to 1200 ppm $CO_2$.
Figure 11B:
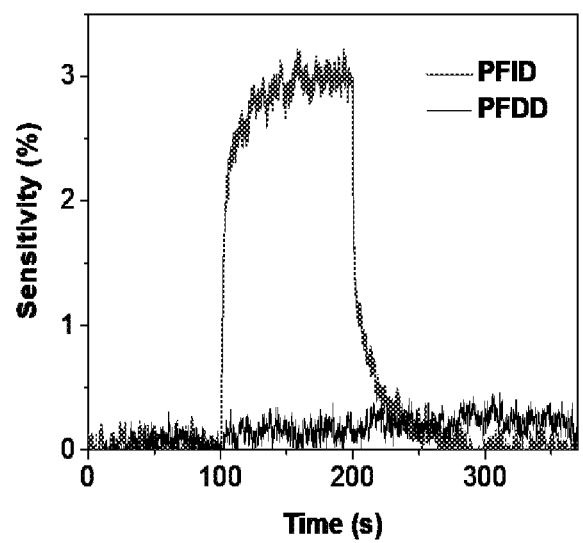

In comparison, the sensor based on bare CNTs, i.e poly (9,9-di-n-dodecylfluorene (PFDD) wrapped CNTs) showed very little response up to 2000 ppm $CO_2$ with a sensitivity of less than 0.1% (see FIG. 11a). Another set of test results is shown in FIG. 11b where the sensor based on poly(9,9-di-n-dodecylfluorene) (PFDD) wrapped CNTs showed very little response to 1200 ppm $CO_2$ in air with RH~40% and contrasted directly with the PFID functionalized CNTs. The sensor with PFID only (no CNT nanotubes) didn't exhibit any signal due to the large resistance.

Sensors with polyethylene imine (PEI) functionalized CNTs require starch polymers to facilitate the reaction between PEI and $CO_2$ by attracting more water (A. Star, T. R. Han, V. Joshi, J. C. P. Gabriel and G. Gruner, Adv. Mater., 2004, 16, 2049). Therefore, this kind of sensor is susceptible to the working environment. For comparison, the present sensors with PFIDBu (IV) functionalized CNTs work well in dry air and show similar sensitivity with PEI/starch-functionalized CNTs sensors. The indigo/CNTs-based sensor of Dubois (Journal of Colloid and Interface Science 407 (2013) 39-46) and the PFO/CNTs-based sensor in Example 1 of US 2017/0200898 did not show any $CO_2$ sensor performance. The novel features will become apparent to those of skill in the art upon examination of the description. It should be understood, however, that the scope of the claims should not be limited by the embodiments, but should be given the broadest interpretation consistent with the wording of the claims and the specification as a whole.

The invention claimed is:
1. A carbon dioxide sensor comprising:
an electrode pair; and,
an electrically conductive sensing material in contact with the electrode pair, the sensing material comprising a film of carbon nanotubes functionalized with a compound of Formula (I):

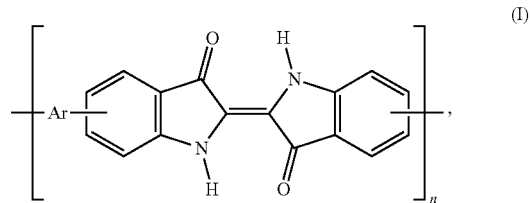

where Ar is a 9,9-dialkyl-substituted fluorene, and n is integer in a range of 20-50, the compound of Formula (I) having a number average molecular weight (Mn) in a range of 10,000 to 50,000 Da and interacting with carbon dioxide to change electrical conductance of the carbon nanotubes by an amount that correlates to carbon dioxide concentration.

2. The carbon dioxide sensor of claim 1, wherein the Ar is at 7 and 7' positions in the compound of Formula (I).

3. The carbon dioxide sensor of claim 1, wherein the carbon nanotubes are single-walled carbon nanotubes.

4. The carbon dioxide sensor of claim 1, wherein the Ar is a 9,9-di$C_{10-36}$-alkyl-substituted fluorene.

5. The carbon dioxide sensor of claim 1, wherein the Ar is a 9,9-di$C_{10-18}$-alkyl-substituted fluorene.

6. A process for producing a compound of Formula (I) as defined in claim 1, the process comprising thermally decomposing a compound of Formula (Ia):

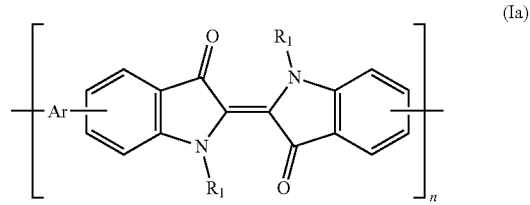

at a temperature of 160° C. or greater, where Ar and n are as defined for the compound of Formula (I) and each $R_1$ is a thermocleavable protecting group.

7. The process of claim 6, wherein the temperature is in a range of 160° C. to 350° C.

8. The process of claim 6, wherein $R_1$ is t-butyloxycarbonyl.

9. The process of claim 6, wherein $R_1$ is an alkyloxycarbonyl group.

10. The process of claim 6, wherein $R_1$ is a $C_{1-4}$ alkyloxycarbonyl group.

* * * * *